United States Patent [19]

DeLuca et al.

[11] Patent Number: 5,430,196
[45] Date of Patent: Jul. 4, 1995

[54] PREPARATION OF 19-NOR VITAMIN D COMPOUNDS

[75] Inventors: Hector F. DeLuca, Deerfield; Heinrich K. Schnoes; Fariba Aria, both of Madison, all of Wis.

[73] Assignee: Wisconsin Alumni Research Foundation, Madison, Wis.

[21] Appl. No.: 302,399

[22] Filed: Sep. 8, 1994

Related U.S. Application Data

[63] Continuation of Ser. No. 926,829, Aug. 7, 1992, abandoned.

[51] Int. Cl.⁶ .................... C07C 43/02; C07C 35/24
[52] U.S. Cl. .................... 568/665; 568/374; 568/819; 552/653
[58] Field of Search .................... 568/374, 819, 665; 552/653

[56] References Cited

U.S. PATENT DOCUMENTS 5,086,191  2/1992  DeLuca et al.

FOREIGN PATENT DOCUMENTS

0387077A1  12/1990  European Pat. Off.
0516410A2  12/1992  European Pat. Off.

OTHER PUBLICATIONS

Solladie and Hutt "Total Synthesis of Dihydroxyvitamin DHV3 and Dihydrotachysterol DHT3", J. Org. Chem. 1987, 52, 3560–3566.
Walborsky and Wust. "Titanium-Induced Reductive Elimination, Syntheses of 1,3-Dienes", J. Am. Chem. Soc. 1982, 104, 5807–5808.
Imamoto, Tsuneo et al, "Organocerium Reagents, Nucleophilic Addition to Easily Enolizable Ketones", Tetrahedrom Letters, vol. 25, No. 38, pp. 4233–4236, 1984.
Perlman, Kato et al, "1α-25-Dihydroxy-1-9-Nor-Vitamin D3, A Novel Vitamin D-Related Compound With Potential Therapeutic Activity" Tetrahedron Letters, vol. 31, No. 13, pp. 1823–1824, 1990.
Perlman, Kato et al, "Novel Synthesis of 19-Nor-Vitamin D Compounds", Tetrahedron Letters, vol. 32, No. 52, pp. 7663–7666, 1991.

*Primary Examiner*—Alan Siegel
*Attorney, Agent, or Firm*—Andrus, Sceales, Starke & Sawall

[57] ABSTRACT

A synthesis of 1α-hydroxy-19-nor-vitamin D compounds comprises (a) the construction of a 5,8-diol-6-yne intermediate by joining ring-A and ring-C/D portions of the desired end product via the condensation of an acetylenic derivative containing the C/D-ring portion of the desired end product with a cyclic dihydroxy ketone representing the A-ring of the desired end product; (b) the partial reduction of the 6,7 acetylenic triple bond linkage between the A and C/D ring potions to obtain a 5,8-diol-6-ene intermediate; and (c) the reductive removal of the 5,8-oxygen functions to generate the required 5,7-diene end product from which the desired 7-trans(7E)-isomer is purified directly, or after optional double bond isomerization of the 7-cis(7Z)-isomer employing a novel thiophenol-promoted isomerization step.

6 Claims, No Drawings

PREPARATION OF 19-NOR VITAMIN D COMPOUNDS

This invention was made with United States Govenment support awarded by the National Institutes of Health (NIH). Grant No. DK-14881. The United States Govenment has certain rights to this invention.

This invention was made in the course of research supported by funds from the U.S. government. invention relates to vitamin D compounds, specifically to a new process for the preparation of 1α-hydroxy-19-norvitamin D analogs and to novel synthetic intermediates.

This application is a continuation of application Ser. No. 07/926,829 filed Aug. 7, 1992, now abandoned.

BACKGROUND OF THE INVENTION

19-Nor-vitamin D compounds are vitamin D analogs in which the ring A exocyclic methylene group (carbon 19) typical of all vitamin D compounds has been removed and replaced by two hydrogen atoms. Specifically, these compounds exhibit a selective activity profile with high potency in inducing cellular differentiation, and minimal bone calcification activity. Such a differential activity profile renders these compounds useful for the treatment of malignancies, or the treatment of various skin disorders. Two different methods of synthesis of these 19-nor-vitamin D analogs have been described (Perlman et al. *Tetrahedron Letters* 31, 1823 (1990); Perlman et al. *Tetrahedron Letters* 32, 7663 (1991), and DeLuca et al., U.S. Pat. No. 5,086,191).

A new method for the synthesis of such analogs has now been developed and is disclosed herein. The method takes advantage of the finding of Walborsky and Wüst (*J. Am. Chem. Soc.* 104, 5807, 1982) that 1,4-diol-2-ene compounds can be reduced by low-valent titanium reagents to 1,3-dienes. Solladie and Hutt (*J. Org. Chem.* 52, 3560, 1987) have exploited this type of reduction for the preparation of dihydrotachysterol and dihydrovitamin D compounds.

SUMMARY OF THE INVENTION

For the synthesis of 1α-hydroxy-19-nor-vitamin D compounds, the new method comprises, (a) the construction of a 5,8-diol-6-yne system, joining the ring-A and ring-C/D portions of the desired product as represented by general structure III below; (b) the partial reduction of the acetylenic linkage to obtain a 5,8-diol-6-ene system as depicted by general structure IV; and (c) the reductive removal of the 5,8-oxygen functions to generate the required 5,7-diene product (compound V, below) from which the desired 7-trans(7E)-isomer (compound Va) is purified directly, or after optional double bond isomerization of the 7-cis(7Z)-isomer employing a novel thiophenol-promoted isomerization step.

DETAILED DESCRIPTION OF THE INVENTION

The first step of the new synthesis of 19-nor-vitamin D derivatives involves the condensation of an acetylenic derivative of general structure I (containing the C/D-ring portion of the desired product) with a cyclic dihydroxy ketone of general structure II (representing the A-ring of the desired product).

In these structures, $X_1$, $X_2$, and $X_3$, which may be the same or different, may represent hydrogen or a hydroxy-protecting group, but preferably, for optimal use in the present process, they each represent a hydroxyprotecting group. For $X_1$ and $X_2$ preferred hydroxyprotecting groups are those that are base-stable, but readily removable when desired. Suitable groups are, for example, alkylsilyl- or alkylarylsilyl groups (hereinafter referred to simply as "silyl" groups, e.g. trimethylsilyl, triethylsilyl, dibutylmethylsilyl, diphenylmethylsilyl, phenyldimethylsilyl, diphenyl-t-butylsilyl, etc.) or alkoxyalkyl groups (e.g. methoxymethyl-, ethoxymethyl, methoxyethoxymethyl, etc., or tetrahydropyranyl, tetrahydrofuranyl groups). In the case of $X_3$, suitable protecting groups are the silyl groups and the alkoxyalkyl groups already mentioned, as well as alkyl groups from 1 to 6 carbons (methyl, ethyl, propyl, isopropyl, etc.). The group R in compound I represents a side chain group as further defined below.

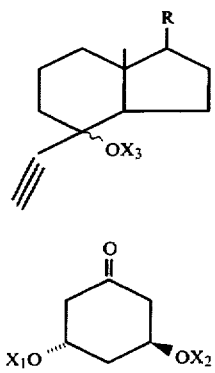

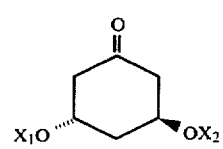

Cyclohexanone derivatives of general structure II are known (Perlman et al. *Tetrahedron Letters* 32, 7663 (1991); acetylenic intermediates of structure I can be prepared by reaction of the corresponding perhydrindene ketones, (C/D-ring-ketones) having the general structure Ia, below, with an acetylenic Grignard reagent and subsequent hydroxy protection (Solladie and Hutt, *J. Org. Chem.* 52, 3560 (1987). The required substituted perhydrindene ketones bearing a diverse range of side chain groups (R) are known or can be prepared by known methods [e.g. Perlman et al., *Tetrahedron Letters* 32, 7663 (1991); Wilson et,al., *J. Org. Chem.* 57, 2007 (1992); Curtin and Okamura, *J. Am. Chem. Soc.* 113, 6958 (1991); Baggiolini et al., *J. Org. Chem.* 51, 3098 (1986); Kiegiel et al., *Tetrahedron Letters* 32, 6057 (1991); Einhorn et al., *Synthesis*, p. 787 (1989); Mascarenas et al. *Tetrahedron Letters* 32, 2813 (1991); Shiiuey et al. *J. Org. Chem.* 55, 243 (1990); Hatekeyama et al. *J.C.S. Chem. Comm.* 1030 (1989)].

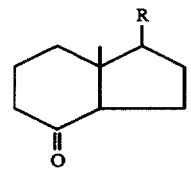

The coupling reaction between the acetylenic intermediate of structure I and the cyclohexanone derivative of structure II requires the conversion of the acetylenic compound to a metal acetylide, which is then allowed to react with the ketone. Thus, the reaction is conducted in an organic solvent, such as an ether or hydrocarbon solvent, at low temperature, and in the presence of a strong organic base (e.g. an alkyl lithium, alkyl lithium amide or analogous strong base). The standard conditions for achieving the condensation of an acetylenic compound with a ketone (e.g. as done in the work of Solladie, supra), typically comprise the treatment of the acetylenic compound with the strong base to produce the lithium acetylide, followed by reaction of the acetylide with the ketone derivative. It was found, however, that such known conditions did not serve for the present synthesis, where the ketone derivative of structure II contains two protected hydroxy groups, which proved to be prone to elimination, yielding undesired products. This difficulty was overcome by conducting the above condensation reaction in the presence of both a strong base (alkyllithium, dialkyllithium amide, etc.) and of a rare earth metal salt, preferably a cerium salt, at low temperature [Imamoto et. al. *Tetrahedron Lett.* 25, 4233 (1984)]. Thus, treatment of the acetylenic intermediate I with an alkyllithium base at low temperature, followed by treatment with cerium chloride, and subsequent reaction with cyclohexanone derivative II, circumvents the undesired elimination reactions, and produces the desired acetylenic coupling product of structure III below, in satisfactory yield. Compounds of general structure III are new compounds.

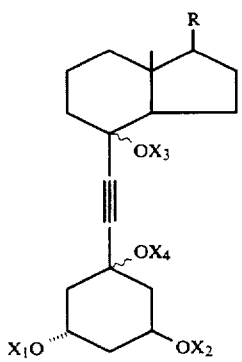

III

The acetylenic coupling intermediate of general structure III above can also be prepared by a novel alternative condensation process, namely by the coupling of a perhydrindene ketone of general structure Ia, above, with an acetylenic ring-A unit, of general structure IIa, below.

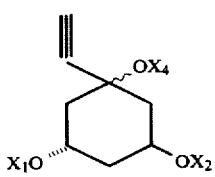

IIa

Acetylenic ring A-synthons of structure IIa, which are new compounds, are prepared by reaction of a cyclohexanone derivative of formula II, above, with a metal acetylide, preferably cerium acetylide, according to the general procedure described above for the condensation of acetylenic intermediate I with ketone II. In compounds of formula IIa, $X_1$ $X_2$ and $X_4$, which may be the same or different, represent hydrogen or a hydroxy-protecting group. For $X_1$ and $X_2$, preferred hydroxy-protecting groups are the silyl and alkoxyalkyl groups, whereas for $X_4$, the preferred groupings include silyl, alkoxyalkyl, and especially also $C_{1-6}$ alkyl groups as previously defined. The coupling between ketone Ia and acetylenic intermediate IIa is effected by converting IIa to the corresponding metal acetylide (e.g. lithium acetylide, or the magnesium haloacetylide) by treatment of IIa with a strong base (e.g. an alkyl lithium, or alkyl lithium amide or similar base, or a alkyl Grignard reagent) in an ether or hydrocarbon solvent at low temperature. Subsequent reaction of this acetylide with the C/D-ketone of general structure Ia, then provides the acetylenic coupling product III, shown above. Alternatively, this coupling reaction may also be conducted in the presence of rare earth metal salts such as cerium salts as described for the reaction between acetylene I and cyclohexanone II, above.

In compound III, as obtained by the condensation of acetylenic derivative I with the cyclohexanone derivative II, the groups $X_1$, $X_2$ and $X_3$ represent hydroxy-protecting groups as originally present in the ketone and acetylenic derivative, respectively, whereas $S_4$ is hydrogen. When compound III is obtained by the coupling of a perhydrindene ketone of general structure Ia with a ring-A acetylenic derivative of formula IIa, the groups $X_1$ $X_2$ and $S_4$ in III represent hydroxy-protecting groups as originally present in acetylene IIa, whereas $X_3$ is hydrogen.

The free hydroxy group in compound III can, however, also be protected, if desired, by any desired hydroxy-protecting group. For example, compound III, where $X_4=H$, can be alkylated by known methods, to yield the derivative where $X_4=$alkyl (e.g. methyl, ethyl, propyl, etc.), or it can be silylated or alkoxyalkylated to derivatives where $S_4$ represents any of the silyl or alkoxyalkyl-protecting groups referred to above. Alternatively, if desired, one or more of the originally present hydroxy-protecting groups ($X_1$, $X_2$, $X_3$) in compound III may be removed by known methods to yield derivatives of III where one or more of $X_1$, $X_2$, $X_3$ represent hydrogen. For example, compound III, where $X_1$, $X_2$, $X_3$ represent alkylsilyl groups and $X_4$ is hydrogen, can be hydrolyzed by known methods to obtain the compound where all of $X_1$, $X_2$, $X_3$ and $X_4$ represent hydrogen. Likewise, if compound III is obtained such that, for example, $X_1$ and $X_2$ represent silyl groups, $X_3$ is alkyl and $S_4$ is hydrogen, it can be hydrolyzed under known conditions to the partially deprotected compound III, where $X_1$, $X_2$ and $X_4$ are hydrogen and $X_3$ is alkyl. Also, derivatives of compound III, e.g. where $X_1$, $X_2$ and $X_3$ are silyl or alkoxyalkyl groups and $S_4$ is alkyl can be hydrolyzed to obtain a product where $X_1$, $X_2$, and $X_3$ represent hydrogen and $X_4$ is alkyl, and any free hydroxy groups in such a product can, of course, also be reprotected to obtain, for example, the derivative of structure III, where $X_1$ and $X_2$ represent silyl or alkoxyalkyl groups, $X_3$ is hydrogen, and $X_4$ is alkyl. Thus, it is obvious that by suitable choice of protecting groups in the A-ring and C/D-ring starting materials (subjected to the coupling reaction) and by optional subsequent protection or deprotection reactions or combinations thereof, intermediate III can be obtained as the free tetraol or in arty desired partially or completely hydroxy-protected form. In general, derivatives of compound III, where $X_1$ and $X_2$, independently, represent hydrogen or a hydroxy-protecting group selected from alkoxyalkyl or silyl, and where $X_3$ and $X_4$, independently represent hydrogen or a hydroxy-protecting group selected from alkoxylalkyl, silyl or alkyl are suitable for the subsequent steps of the process. Preferred derivatives are the compounds where $X_1$ and $X_2$ are both hydrogen, and where $X_3$ and $S_4$ are both hydrogen or both alkyl, or where one of $X_3$ and $S_4$ is hydrogen, the other alkyl.

The next step of the process comprises the partial reduction of the 6,7-triple bond in compound III to obtain the corresponding 6,7-olefinic compound, characterized by general structure IV below.

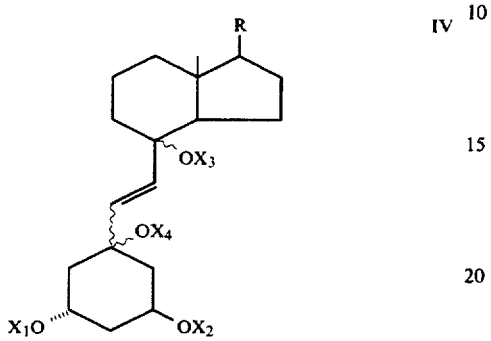

Depending on the reduction conditions employed, the product IV obtained in this step may have either the 6,7-cis or the 6,7-trans double bond configuration. Thus, reduction of compound III (where each of $X_1$, $X_2$, $X_3$, $X_4$, which may be the same or different, represent hydrogen or a hydroxy-protecting group as defined above) with hydrogen in the presence of palladium catalyst yields the 6,7-cis product IVa (where each of $X_1$, $X_2$, $X_3$, $S_4$ may represent hydrogen or a hydroxy-protecting group).

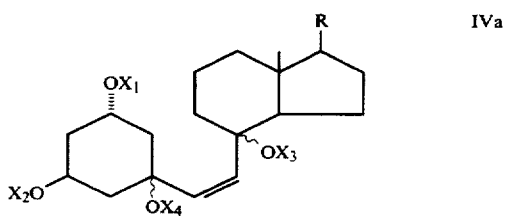

Alternatively, compound III may be reduced with hydride reducing agents in an organic solvent (e.g. LiAlH$_4$, etc., in an ether solvent) to obtain the 6,7-trans-ene product characterized by structure IVb, below (where $X_1$, $X_2$, $X_3$, $S_4$ represent hydrogen or hydroxy-protecting groups as previously defined).

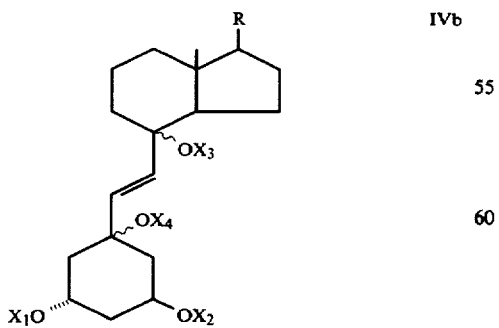

Products of type IVa or IVb are new compounds, and both of these intermediates are suitable for further conversion to the desired final product.

Intermediate IV, as obtained above (i.e. either the 6,7-cis isomer IVa or the corresponding trans-isomer IVb) is then subjected to a further reduction step, using a low-valent titanium reducing agent of the type employed in the work of Walborsky and Wüst, supra. Thus, treatment of intermediate IV (where each of $X_1$, $X_2$, $X_3$, $X_4$, independently, represent hydrogen or a hydroxy-protecting group and where the double bond configuration may be cis or trans) with mixtures of titanium chloride and a metal hydride in an organic solvent yields the 5,7-diene product of general structure V (where $X_1$ and $X_2$ represent independently hydrogen or hydroxy-protecting groups as defined for the precursor III) as a mixture of 7,8-cis and 7,8-trans-double bond stereoisomers.

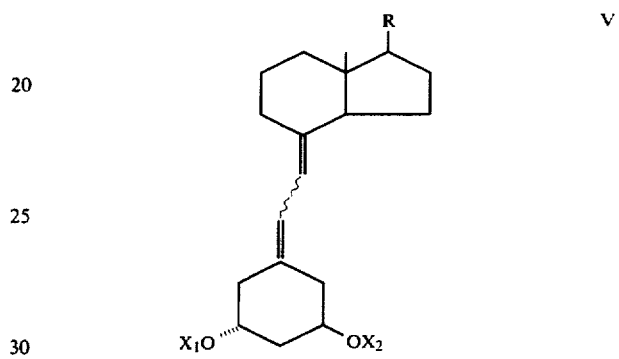

It has also been found that product V (as a mixture of the 7,8-cis and trans isomers) can be obtained in a single step from the acetylenic coupling intermediate III by reaction with a metal hydride/titanium reducing agent. For example, direct treatment of III with the low-valent titanium reagent prepared by reacting a metal hydride with titanium chloride provides the 5,7-diene product V as a mixture of 7,8-cis and 7,8-trans-stereoisomers. Thus, the conversion of III to V can be accomplished by the two alternative two-step procedures described above, as well as this one-step method. Best yields have been obtained with the two-step sequence involving catalytic hydrogenation, followed by reduction with metal hydride/titanium reagent.

The mixture of 7,8-cis- and 7,8-trans-isomers may be separated by chromatography (preferably high performance liquid chromatography) to obtain separately the 7,8-trans-isomers, i.e. the known 1α-hydroxy-19-nor-vitamin D compounds characterized by structure Va and the 7,8-cis-isomer, represented by structure Vb, wherein $X_1$ and $X_2$ represent hydrogen or hydroxy-protecting groups.

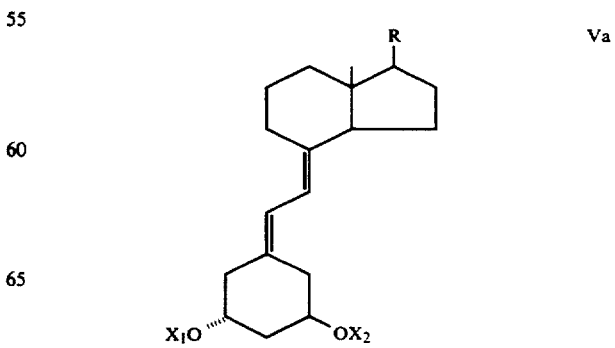

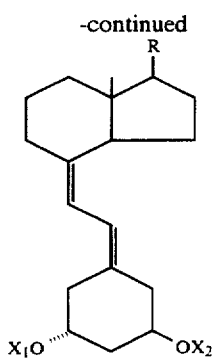

The 7,8-cis-isomers of general structure Vb are new compounds. Any hydroxy-protecting groups present in compounds Va or Vb can, of course, be removed by conventional methods to obtain the corresponding free hydroxy compounds, i.e. Va and Vb where both $X_1$ and $X_2$ represent hydrogen.

The 7,8-cis-isomers of general structure Vb can also serve as useful intermediates for the production of the 7,8-trans compounds of structure Va. It has been found that treatment of the cis-isomer Vb with a thiol reagent (e.g. thiophenol) isomerizes the 7,8-cis double bond to yield the corresponding 7,8-trans isomer Va. This isomerization reaction can be performed on isolated 7,8-cis-isomer, but preferably, especially when the 7,8-trans isomer Va is desired as the sole final product of the present process, the isomerization is performed directly on the original mixture of the 7,8-cis- and 7,8-trans-isomers. Thus treatment of the intermediate product mixture V (where $X_1$ and $X_2$, independently, represent hydrogen or hydroxy-protecting groups) as obtained from the titanium reduction step, with a thiol in an organic solvent yields specifically the 7,8-trans-isomer Va. Any hydroxy-protecting groups, if present, can then be removed by conventional methods to obtain 1α-hydroxy-19-nor-vitamin D product (compound Va, where $X_1$ and $X_2$ represent hydrogen). The above described isomerization reaction using thiol reagents is essentially quantitative, and provides a convenient method for the conversion of 7,8-cis-isomers of the vitamin D series to their (generally desired) 7,8-trans-isomeric forms.

The side chain group R in any of the above-shown structures, i.e. in structures I, III, IV, and V may represent any of the presently known steroid side chain types. More specifically R can represent a saturated or unsaturated hydrocarbon radical of 1 to 35 carbons, that may be straight-chain, branched or cyclic and that may contain one or more additional substituents, such as hydroxy- or protected-hydroxy groups, fluoro, carbonyl, ester, epoxy, amino or other heteroatomic groups. Preferred side chains of this type are represented by the structure below.

where the stereochemical center (corresponding to C-20 in steroid numbering) may have the R or S configuration, (i.e. either the natural configuration about carbon 20 or the 20-epi configuration), and where Z is selected from the group consisting of Y, —OY, —CH$_2$OY, —C≡CY and —CH=CHY, where the double bond may have the cis or trans geometry, and where Y is selected from the group consisting of hydrogen, methyl, —CR$^5$O and a radical of the structure,

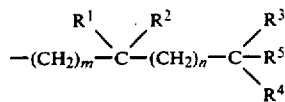

where m and n, independently, represent the integers from 0 to 5, where $R^1$ is selected from the group consisting of hydrogen, hydroxy, protected hydroxy, fluoro, trifluoromethyl, and $C_{1-5}$-alkyl, which may be straight chain or branched and, optionally, bear a hydroxy or protected-hydroxy substituent, and where each of $R^2$, $R^3$, and $R^4$, independently, is selected from the group consisting of hydrogen, fluoro, trifluoromethyl and $C_{1-5}$ alkyl, which may be straight-chain or branched,, and optionally, bear a hydroxy or protected-hydroxy substituent, and where $R_1$ and $R^2$, taken together, represent an oxo group,, or an alkylidene group, =CR$^2$R$^3$, or the group —(CH$_2$)$_p$—, where p is an integer from 2 to 5, and where $R^3$ and $R^4$, taken together, represent an oxo group, or the group —(CH$_2$)$_q$—, where q is an integer from 2 to 5, and where $R^5$ represents hydrogen, hydroxy, protected hydroxy, or $C_{1-5}$ alkyl.

A "protected hydroxy" group is a hydroxy group protected by any group commonly used for the temporary or permanent protection of hydroxy functions, e.g. the silyl, alkoxyalkyl, or alkyl groups, as previously defined.

Specific embodiments of the reactions of the new process are presented in the following Examples. Process Scheme 1 depicts the structures of the compounds described in these Examples, such that products identified by Arabic numerals (e.g. 1, 2, 3, 3a, etc.) correspond to the structures so numbered in the Process Scheme. The abbreviation "TBS" signifies a t-butyldimethylsilyl hydroxy-protecting group.

EXAMPLES

Example 1

Preparation of Acetylenic 5,8-Diol Intermediate, Compound 3

Cerium chloride (275 mg; 1.1 mmol) was dried with stirring at 140° C. in vacuo (0.01 torr) for 2 h and cooled, dry tetrahydrofurane (3 ml) was added with stirring under argon and stirring was continued for 2 h. The resulting suspension was then cooled to −78° C. and CD-ring lithium acetylide [prepared by addition of 0.56M BuLi (1.98 ml) to a THF solution (340 mg, 1.1 mmol) of CD ring acetylene (compound 1) at room temperature (RT)] was added. The color of the suspension turned yellow; stirring was continued for 30 min at the same temperature. Then 3,5-trans-dihydroxychlohexanone compound 2(200 mg, 0.55 mmol) in tetrahydrofuran (3 ml) was added. The mixture was stirred for 15 min, treated with sat. aqueous solution of NH$_4$Cl and extracted with ether (3×50 ml). The combined extracts were washed with brine (20 ml), dried over MgSO$_4$, concentrated in vacuo and the residue was purified by flash chromatography on silica gel to give 322 mg, 87%, of product 3.

NMR 1H (CDCl$_3$), δ ppm, 0.05, 0.06, 0.07 (TBS-Me), 0.84 (26, 27, 21, 18 Me), 0.87 (s, TBS-Me), 1.72 (dd, J=14.49 Hz, J=2.22 Hz, 1H), 1.90 (d, J=12.62 Hz, 1H), 1.99 (d, J=12.66 Hz, 1H), 2.10 (d, J=14.3 Hz, 1H), 2.18 (d, J=14.14 Hz, 1H), 2.35 (d, m, J=13.25 Hz, 1H), 3.24 (s, 3H, OMe), 4.22 (ddd, J=14.66 Hz, J=9.33 Hz, J=4.0 Hz, 1H, H-3), 4.28 (ls, 1H, H-1), 4.58 (s, 1H, OH). MS: m/e (relative intensity), 662 (M+, 14%), 644 (28%), 630 (27%), 605 (5%), 301 (20%), 143 (53%), 75 (100%).

Example 2

Hydrolysis of 3 to 3a

To a solution of 3 (81.5 mg; 0.12 mmol) in THF (4 ml) was added HF 48% (0.5 ml). The mixture was stirred at RT for 30 min, neutralized with saturated solution of sodium bicarbonate and extracted with $CH_2Cl_2$ (3×20 ml). Combined organic layer was dried over $MgSO_4$ and concentrated. The product, compound 3 was used without further purification for the next reaction.

$^1$H NMR (CDCl$_3$) δ ppm: 0.84, 0.85, 0.86 (3s, 12H), 2.15 (m, 3H), 2.32 (dm, J=9.97 Hz, 1H), 2.89 (ls, 1H), 3.24 (s, 3H), 4.21 (m, 1H), 4.27 (m, 1H).

Example 4

Catalytic Hydrogenation of 3a to 4a

To a solution of triol of 3a (53 mg, 0.12 mmol) in MeOH (4 ml) was added quinoline (11.5 μl, 0.09 mmol) and Lindlar catalyst (57 mg=0.02 mmol), stirred under a hydrogen atmosphere at RT for 45 min. The reaction mixture was filtered over celite using ethylacetate for washing. Purification on silica-gel using EtoAc/hexane (4:1) gives 48.11 mg of pure product compound 4a. Yield from 3a, 90%.

$^1$H NMR (CDCl$_3$) δ ppm: 0.83, 0.84, 0.86, 0.87 (4s, 12H), 1.97 (dm, J=13.74 Hz, 2H), 2.09 (dm, J=14.67 Hz, 1H), 2.20 (dm, J=14.67 Hz, 1H), 2.29 (dm J=12.83 Hz, 1H), 3.27 (s, 3H, OMe), 4.14 (m, 1H), 4.36 (m, 1H), 4.75 (d, J=9.69 Hz, 1H), 4.90 (d, J=13.5 Hz, 1H), 5.20 (d, J=13.55 Hz, 1H), 7.11 (s, 1H, OH). MS: m/e (relative intensity): 436 (M+, 18%), 418 (9%), 404 (48%), 361 (100%), 345 (15%), 302 (15%), 247 (11%), 195 (12%), 147 (13%), 95 (18%), 81 (19%), 55 (27%), 43 (45%).

Example 5

1α-Hydroxy-7(E&Z)-19-nor-vitamin D$_3$ 5a and 5b.

To a solution of TiCl$_3$ (268 mg, 1.73 mmol) in dry THF (1.4 ml) under argon was added 1M solution of LAH in ether (0.68 ml, 0.68 mmol) at RT, a black suspension formed, stirred for 30 min. Then a solution of triol 4a (16 mg; 0.036 mmol) in THF (0.7 ml) was added, heated at reflux for 3 h, cooled to RT, then hydrolyzed slowly with cold 1M HCl (10 ml). The mixture was extracted with ether (1×20 ml) and $CH_2Cl_2$ (2×20 ml). Combined organic layers were washed with saturated solution of sodium bicarbonate (10 ml), dried over $MgSO_4$ and concentrated, to obtain 5,7-diene compound 5a and 5b (2:3). This product was used for the isomerization reaction without further purification.

$^1$H NMR: (CDCl$_3$), δ: 0.52, 0.62 (2s, 3H, 18-Me), 0.85 (2d, J=6.77 Hz, J=5.25 Hz, 6H), 0.9 and 0.91 (2d, J=6.14 Hz, 5.1 Hz, 3H), 2.72 & 2.75 (2 dm, J=9.32 Hz & J=10.33 Hz, 1H), 4.03 (m, 1H), 4.09 (m, 1H), 5.83 and 6.09 (2d, J=11.19 Hz and J=11.3 Hz, 1H), 6.29 and 6.46 (2d, J=11.22 Hz and J=11.63 Hz, 1H).

Example 6

Isomerization of 5b to 5a

To the product (mixture of 5a/5b) as obtained in Example 5 was added $CH_2Cl_2$ (8 ml) and thiophenol (1 μl, 0.0097 mmol) at RT, stirred for 1 h. The isomerization was monitored by HPLC [reversed phase, MeOH:water (9:1)]. Complete isomerization is observed after 1 h. Solvent was removed under vacuum at RT, then silica gel chromatography using EtoAc:hexane (4:1) gives 5a; yield=75% from 4a.

$^1$H NMR (CDCl$_3$) δ ppm: 0.52 (s, 3H, 18-Me), 0.85 (d, J=6.50 Hz, 6H, 26,27-Me), 0.90 (d, J=6.05 Hz, 3H, 20-Me), 2.19 (m, 2H), 2.46 (dm, J=13.27 Hz, 1H), 2.72 (dd, J=13.17 Hz, J=3.60 Hz, 1H), 2.78 (dm, J=12.85 Hz, 1H), 4.02 (m, 1H), 4.10 (m, 1H), 5.83 (d, J=10.98 Hz, 1H), 6.29 (d, J=11.2 Hz, 1H). MS: m/e (relative intensity): 388 (M+, 100%), 275 (33%), 247 (30%), 180 (21%), 133 (38%), 95 (52%), 81 (43), 55(46%), 43 (81%). UV EtOH λ$_{max}$: 261 (21000), 251.1 (31000), 242.6 (26000).

Example 7

Hydride Reduction of 3a to 4b

To a solution of acetylenic alcohol 3a (24.7 mg, 0.059 mmol) in ether (1 ml) at 0° C. was added 1M solution of LAH in THF (262 μl, 0.26 mmol). The mixture stirred at 0° C. for 1 h, quenched with 1M HCl (10 ml) and extracted with ether (3×10 ml). Combined organic layers were washed with brine (5 ml), dried over $MgSO_4$ and concentrated to yield product 4b.

$^1$H NMR (CDCl$_3$) δ ppm, 0.85 (26,27,21,18-Me), 3.24 (s, 3H), 4.21 (m, 1H), 4.27 (m, 1H), 5.51 (2d, AB system, J=15.5 Hz, 2H).

Example 8

1α-Hydroxy-7(E&Z)-19-Nor-Vitamin D$_3$ 5a and 5b from 4b.

A solution of TiCl$_3$ (109 mg, 0.707 nmol) in THF (2 ml) was treated with 1M solution of LAH (353 μl, 0.35 mmol), a black suspension formed that was stirred for 30 min at RT. A solution of product 4b as obtained in Example 7 (0.057 mmol) in THF (2 ml) was added, stirred at RT for 30 min, then refluxed for 1 h, cooled to RT for 5 more h, quenched with 1M HCl (10 ml), extracted with ether (2×30 ml). Combined organic layers were washed with water (10 ml) and brine (10 ml), dried over $MgSO_4$ and concentrated under vacuum. Silica gel chromatography of residue using MeOH/$CH_2Cl_2$ (1:9) gave 3.63 mg of mixture of dienes 5a. (and 5b); (16%) from 3a.

$^1$H NMR (300 MHz) (CDCl$_3$) δ ppm: 0.52, 0.62 (2S, 3H, 18-Me), 0.85 (d, J=6.45, 6H), 0.9 (m, 3H), 2.72, 2.75 (m, 1H), 4.03 (m, 1H), 4.09 (m, 1H), 5.83 and 6.09 (2d, J=11.2 Hz, J=11.3 Hz, 1H), 6.29 and 6.45 (2d, J=11.2 and J=11.3 Hz, 1H).

Example 9

1α-Hydroxy-7(E&Z)-19-Nor-Vitamin D$_3$ 5a and 5b from 3a

A solution of TiCl$_3$ (266 mg, 1.73 mmol) in THF (5 ml) was treated at RT with 1M solution of LAH in THF (860 μl, 0.86 mmol) for 30 min. To the resulting black suspension was added at 0° C. triol of 3a (53 mg, 0.123 mmol) in THF (3 ml). The mixture was refluxed for 8 h, cooled to RT, stirred for 12 h, then quenched with 1N HCl (50 ml) and extracted with CH2Cl2 (3×50 ml). Organic layers were combined, washed with saturated solution of NaHCo3 (20 ml), brine (20 ml), dried over MgSo4 and concentrated under vacuum. Silica gel TLC preparative chromatography of residue gave 8.25 mg of mixture of 5a and 5b (17%).

1H NMR 500 MHz (CDCl3), δ ppm: 0.52, 0.62 (2S, 3H, 18-Me), 0.85 (2d, J=6.8 Hz and J=5.2 Hz, 6H), 0.9 and 0.91 (2d, J=6.14 Hz, J=5.1 Hz, 3H), 2.72, 2.75 (2dm, J=9.32 Hz & J=10.33 Hz, 1H), 4.03 (m, 1H), 4.09 (m, 1H), 5.83 and 6.09 (2d, J=11.04 Hz and J=11.61 Hz, 1H), 6.29 and 6.46 (2d, J=11.12 Hz, J=11.56 Hz, 1H).

Example 10

Catalytic Hydrogenation of 3 to 4c

To a solution of compound 3 (7 mg, 0.01 mmol) in MeOH (0.3 ml) was added quinoline (1 μl, 0.007 mmol) and Lindlar catalyst (1.1 mg, 0.0005 mmol), stirred under hydrogen atmosphere at room temperature for 15 hr. The reaction mixture was filtered over celite and concentrated. Purification of residue on silica gel using ethylacetate:hexane (5:95) gave 4.77 mg of pure 4, yield 68%.

1H NMR (CDCl3 δ ppm, 0.02, 0.03, 0.08 (TBS-Me), 1.82 (m, 1H), 1.92 (m, 1H), 2.11 (m, 1H), 3.21 (s, 3H), 4.14 (m, 1H), 4.20 (m, 1H), 4.91 (d, J=14.22 Hz, 1H), 5.65 (d, J=14.19 Hz, 1H), 6.02 (ls, 1H).

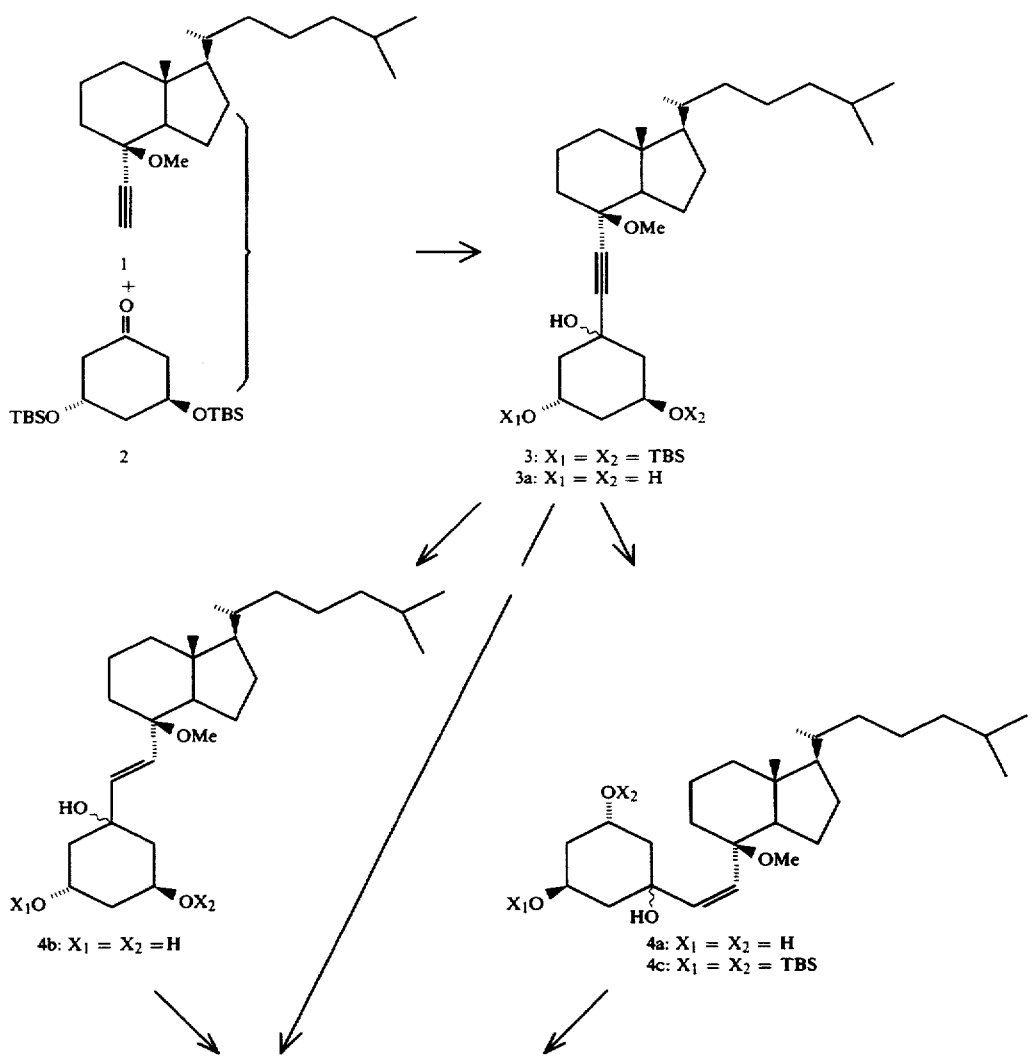

Process Scheme 1

-continued
Process Scheme 1

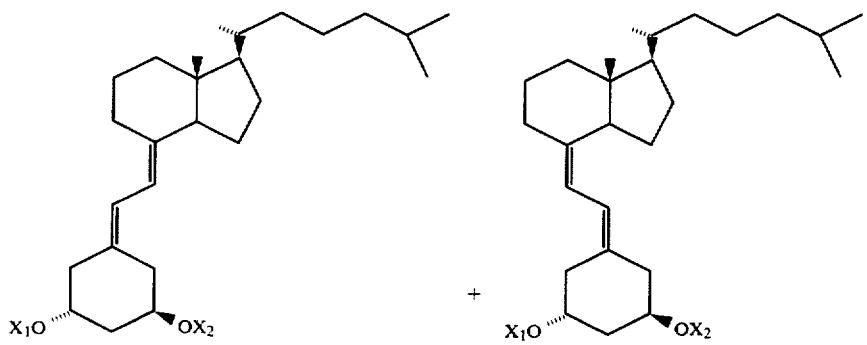

5a: $X_1 = X_2 = H$

5b: $X_1 = X_2 = H$

We claim:

1. Compounds of the formula.

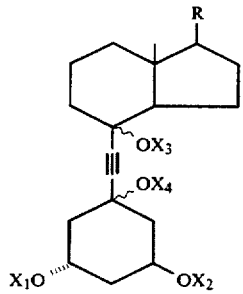

where R is represented by the structure

where the stereochemical center at carbon 20 in the side chain may have the R or S configuration, and where Z is selected from the group consisting of Y, —OY, —CH$_2$OY, —C≡CY and —CH═CHY, where the double bond may have the cis or trans stereochemical configuration, and where Y is selected from the group consisting of hydrogen, methyl —CR$^5$O and a radical of the structure

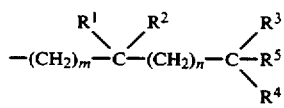

where m and n, independently, represent the integers from 0 to 5, where R$^1$ is selected from the group consisting of hydrogen, hydroxy, protected hydroxy, fluoro, trifluoromethyl, and C$_{1-5}$ alkyl, which may be straight chain or branched and, optionally, bear a hydroxy or protected-hydroxy substituent, and where each of R$^2$, R$^3$ and R$^4$, independently, is selected from the group consisting of hydrogen, fluoro, trifluoromethyl and C$_{1-5}$ alkyl, which may be straight-chain or branched, and optionally, bear a hydroxy or protected-hydroxy substituent, and where R$^1$ and R$^2$, taken together, represent an oxo group, or an alkylidene group, ═CR$^2$R$^3$, or the group —(CH$_2$)$_p$—, where p is an integer from 2 to 5, and where R$^3$ and R$^4$, taken together, represent an oxo group, or the group —(CH$_2$)$_q$— where q is an integer from 2 to 5, and where R5 represents hydrogen, hy-droxy, protected-hydroxy, or C$_{1-5}$ alkyl, and where X$_1$, X$_2$, and X$_4$ each represent, independently, hydrogen or a hydroxy-protecting group and X$_3$ represents hydrogen, methyl or a hydroxy-protecting group.

2. The compounds of claim 1 where R is a side chain of the formula:

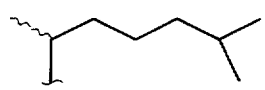

and X$_1$, X$_2$, X$_3$ and X$_4$ are as defined in claim 1.

3. The compounds of claim 1 where R is a side chain of the formula:

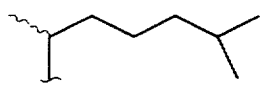

X$_1$, X$_2$, and X$_3$ are hydroxy-protecting groups, and X$_4$ is hydrogen.

4. The compounds of claim 1 where R is a side chain of the formula:

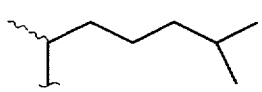

X$_1$, X$_2$, and S$_4$ are hydroxy-protecting groups, and X$_3$ is hydrogen.

5. The compounds of claim 1 where R is a side chain of the formula:

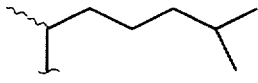

X$_1$ and X$_2$ are both 5-butyldimethylsilyl, X$_3$ is methyl and X$_4$ is hydrogen.

6. The compounds of claim 1 where R is a side chain of the formula:

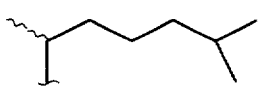

X$_1$, X$_2$, and X$_4$ are all hydrogen and X$_3$ is methyl.

* * * * *

UNITED STATES PATENT AND TRADEMARK OFFICE
CERTIFICATE OF CORRECTION

PATENT NO. : 5,430,196
DATED : July 4, 1995
INVENTOR(S) : Hector F. DeLuca et al It is certified that error appears in the above-indentified patent and that said Letters Patent is hereby corrected as shown below:

Claim 1, Col. 14, Line 20      Delete "$Cl_{1-5}$" and substitute therefor ---$C_{1-5}$---.

Claim No. 4, Col. 14, Line 49      After "and" delete "$S_4$" and substitute therefor ---$X_4$---.

Signed and Sealed this

Sixteenth Day of January, 1996

*Attest:*

BRUCE LEHMAN

*Attesting Officer*      *Commissioner of Patents and Trademarks*